United States Patent [19]
Banfi et al.

[11] 4,173,569
[45] Nov. 6, 1979

[54] PREPARATION OF PYRROLIDINE AND PYRROLIDIN-2-ONE DERIVATIVES

[75] Inventors: Silvano Banfi, Paderno Dugnano; Renato Pellegata; Giorgio Pifferi, both of Milan; Mario Pinza, Corsico, all of Italy

[73] Assignee: I.S.F. SpA, Milan, Italy

[21] Appl. No.: 876,169

[22] Filed: Feb. 8, 1978

[30] Foreign Application Priority Data

Feb. 11, 1977 [IT] Italy .............................. 20227 A/77

[51] Int. Cl.² ......................................... C07D 207/26
[52] U.S. Cl. ....................... 260/326.43; 260/326.5 C; 260/326.5 M; 424/274
[58] Field of Search .................................... 260/326.43

[56] References Cited
FOREIGN PATENT DOCUMENTS 2635853 2/1977 Fed. Rep. of Germany .
2635854 2/1977 Fed. Rep. of Germany .

OTHER PUBLICATIONS

Aantaa, E., et al, J. Int. Med. Res., (1975) 3, pp. 352-356.

Primary Examiner—Donald G. Daus
Assistant Examiner—Lisa Jones
Attorney, Agent, or Firm—Stevens, Davis, Miller & Mosher

[57] ABSTRACT

Preparation of compounds of the formula:

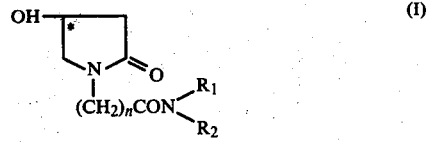

(I)

wherein n is 1, 2 or 3, $R_1$ and $R_2$, which may be the same or different, are hydrogen or alkyl containing 1 to 3 carbon atoms and the asterisk indicates the center of asymmetry of the molecule, and compounds of the formula

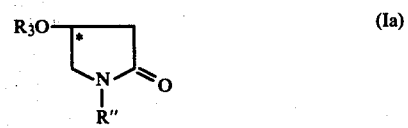
(Ia)

wherein R" is a saturated or unsaturated aliphatic hydrocarbon containing 1 to 6 carbon atoms, $R_3$ is hydrogen or acyl containing 1 to 7 carbon atoms and the asterisk indicates the center of asymmetry of the molecule. The compounds produced by the present invention improve learning memory and display a protecting effect against the E.E.G. consequence of an overdose of barbiturates and against the reduced performance following brain damage (e.g. cerebral edema).

3 Claims, No Drawings

PREPARATION OF PYRROLIDINE AND PYRROLIDIN-2-ONE DERIVATIVES

The present invention is concerned with a process for the preparation of pyrrolidine derivatives.

The pyrrolidine derivatives according to the present invention are compounds of the general formula:

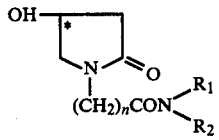

wherein n is 1, 2 or 3, $R_1$ and $R_2$, which may be the same or different, are hydrogen or alkyl containing 1 to 3 carbon atoms and the asterisk indicates the center of asymmetry of the molecule.

The compounds of formula (I), whether in their racemic or optically active form, display activity on the central nervous system and are included in a broader class of compounds described in our U.S. Patent application Ser. No. 713,901, now U.S. Pat. No. 4,118,396. The method for the preparation of these compounds therein described comprises a series of steps, starting from compounds, the preparation of which is complex.

According to the present invention, there is provided a process which, in comparison with the above-mentioned synthesis, enables one to obtain the desired compounds in a reduced number of steps, using simple and convenient starting materials.

According to the present invention, compounds of general formula (I) are prepared from γ-amino-β-hydroxybutyric acid which, after reaction with a silylating agent, is cyclized and subsequently reacted, in the presence of an appropriate base, such as an alkali metal hydride, with a halide derivative of an appropriate ester of an appropriate aliphatic acid to give the corresponding N-carboxyalkyl derivatives which are then converted into the corresponding amides by reaction with ammonia or with an appropriate amine.

The process may be schematically represented as follows:

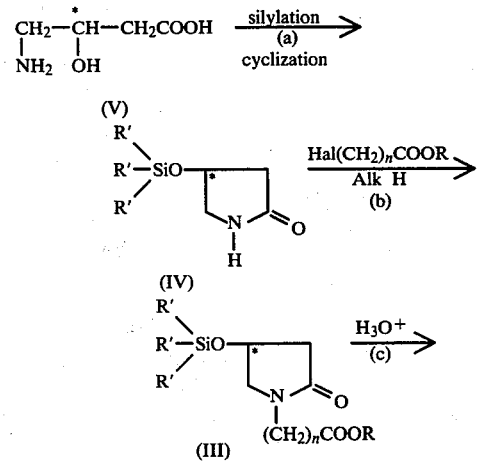

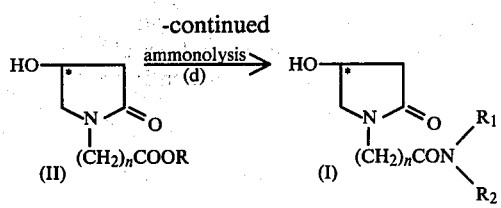

wherein R' is methyl or ethyl, Hal is bromine, chlorine or iodine, R is alkyl containing 1 to 4 carbon atoms or trichlorophenyl, nitrophenyl or trichloroethyl, Alk is sodium, potassium or lithium, the asterisk indicates the center of asymmetry of the molecule, n is 1, 2 or 3 and $R_1$ and $R_2$, which may be the same or different, are hydrogen or alkyl containing 1 to 3 carbon atoms.

Steps (a), (b) and (c) of the above-mentioned process may be carried out without separation of the intermediates, which represents a further simplification when compared with the previously known process.

γ-Amino-β-hydroxybutyric acid (V) is treated under anhydrous conditions in an inert aprotic solvent, such as toluene, acetonitrile, dioxane and xylene, with an excess of a silylating agent at the boiling point of the solvent employed and the cyclized silyloxy derivative (IV) obtained is reacted with a halide derivative of an aliphatic acid ester Hal(CH$_2$)$_n$COOR, wherein Hal, n and R have the same meanings as above, in an aprotic and preferably polar solvent, such as acetonitrile, dimethyl formamide, dioxane, dimethyl sulphoxide or hexamethyl phosphoramide, and then with an alkali metal hydride, such as sodium, potassium or lithium hydride.

The temperature used is not critical for the reaction but is preferably from 35° to 80° C., optionally with refluxing for a short period of time in order to complete the reaction for obtaining the compound (III), from which the silyl protecting group is removed by hydrolysis (step c) to give the corresponding 4-hydroxy derivative (II) from which, by treatment with concentrated ammonia or with a mono- or di-substituted amine NHR$_1$R$_2$, the desired compound (I) is obtained.

The silylating agent may be, for example, hexamethyldisilazane, bis-(trimethylsilyl)-urea or bis-(trimethylsilyl)-acetamide: in practice, the selected silylating agent is preferably employed in the presence of a small quantity of trimethylchlorosilane.

Compounds (I) and (II) can be acylated in a known manner to give the corresponding 4-acyloxy derivatives, the acetic, propionic, butyric, n-valeric, hexanoic, malonic, succinic and benzoic acid derivatives being preferred.

According to the process of the present invention, there can also be prepared compounds of the general formula:

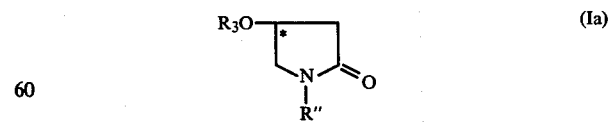

wherein R" is a saturated or unsaturated aliphatic hydrocarbon containing 1 to 6 carbon atoms, the term "saturated or unsaturated aliphatic hydrocarbon" preferably meaning methyl, ethyl, propyl, butyl, pentyl, hexyl, allyl, propargyl or the like, and $R_3$ is hydrogen or acyl containing 1 to 7 carbon atoms.

According to the process of the present invention, schematically represented above, the cyclized silyloxy derivative (IV) is reacted with an alkyl halide of the general formula Hal R", wherein Hal and R" have the same meanings as above, to give, under the conditions described hereinbefore, compounds (IIIa) and (IIa) successively, the process being schematically represented as follows:

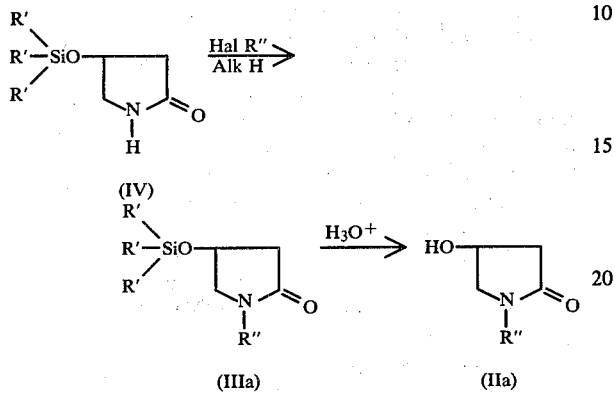

Compounds (IIa) may be acylated in a known manner to give the corresponding O-acyl derivatives, said acyl derivatives containing acetic, propionic, butyric, benzoic, n-valeric, hexanoic, malonic, succinic or the like acid being preferred.

Alternatively, the O-acyl derivatives of compounds (IIa) may be prepared from compounds (IVa) having, in the 4-position, instead of a silyloxy radical, the desired acyloxy radical, by reaction, under the described conditions, with an alkyl halide Hal R", wherein Hal and R" have the same meanings as above.

The following Examples are given for the purpose of illustrating the present invention:

EXAMPLE 1

2-(4-Hydroxypyrrolidin-2-on-1-yl)-acetamide

To a suspension of 10 g. γ-amino-β-hydroxybutyric acid in 200 ml. anhydrous xylene, are added 26.3 ml. hexamethyldisilazane and 3 drops trimethylchlorosilane. The reaction mixture is heated under reflux until the solution is clear and then for an additional 30 minutes. The so obtained solution is evaporated to dryness and the residue is recrystallized from diisopropyl ether to give 13.5 g. 4-trimethylsilyloxypyrrolidin-2-one; m.p. 97°–98° C.; Rf 0.20 (silica gel; eluant ethyl acetate).

To a solution of 51.5 g. 4-trimethylsilyloxypyrrolidin-2-one in 500 ml. anhydrous acetonitrile are added 133 ml. ethyl bromoacetate. The solution is heated to 50° C. and 26.7 g. of 80% sodium hydride (dispersion in mineral oil) are slowly added in small amounts. When the addition is completed, the reaction mixture is heated under reflux for 30 minutes and then cooled to ambient temperature. To the reaction mixture obtained containing ethyl 2-(4-trimethylsilyloxypyrrolidin-2-on-1-yl)-acetate (b.p. 160° C./3 mm.Hg) are added 50 ml. 1 N hydrochloric acid. The reaction mixture is stirred for 30 minutes and then evaporated to dryness. The residue obtained is chromatographed on a silica gel column, using ethyl acetate as the elution agent, 45 g. ethyl 2-(4-hydroxypyrrolidin-2-on-1-yl)-acetate being obtained; b.p. 180° C./0.8 mm.Hg; Rf 0.17 (silica gel; eluant ethyl acetate).

A solution of 7.1 g. ethyl 2-(4-hydroxypyrrolidin-2-on-1-yl)-acetate and 7.1 ml. ammonium hydroxide ($d_{25}$ 0.90) is stirred at ambient temperature for 15 hours. It is then diluted with 140 ml. acetone and stirred at ambient temperature until the gummy precipitate solidifies to form white crystals. By vacuum filtration and drying, there are obtained 5.1 g. 2-(4-hydroxypyrrolidin-2-on-1-yl)-acetamide; m.p. 160°–162° C.; Rf 0.32 (silica gel; eluant acetonitrile:water 4:1 v/v).

EXAMPLE 2

R(+) 2-(4-Hydroxypyrrolidin-2-on-1-yl)-acetamide

Operating is as described in Example 1 and using as the starting material R(−) γ-amino-β-hydroxybutyric acid, there is obtained, via ethyl R(+) 2-(4-hydroxypyrrolidin-2-on-1-yl)-acetate (b.p. 179° C./0.8 mm.Hg.), R(+) 2-(4-hydroxypyrrolidin-2-on-1-yl)-acetamide; m.p. 135°–136° C.; $[\alpha]_D = +36.2$ (water, c+1).

EXAMPLE 3

3-(4-Hydroxypyrrolidin-2-on-1-yl)-propionamide

Operating as described in Example 1 and using as the starting material ethyl 3-bromopropionate instead of ethyl bromoacetate, there is obtained, via ethyl 3-(4-hydroxypyrrolidin-2-on-1-yl)-propionate (b.p. 190° C./0.8 mm.Hg. (dec.)), 3-(4-hydroxypyrrolidin-2-on-1-yl)-propionamide (m.p. 99°–100° C.).

EXAMPLE 4

1-Ethyl-4-benzyloxypyrrolidin-2-one

Operating as described in Example 1 but using ethyl iodide instead of ethyl bromoacetate, there is obtained 1-ethyl-4-hydroxypyrrolidin-2-one (b.p. 160° C./0.8 mm.Hg).

Three g. 1-ethyl-4-hydroxypyrrolidin-2-one are dissolved in 30 ml. anhydrous pyridine and 2.7 ml. benzoyl chloride are added thereto. The reaction mixture is stirred overnight at ambient temperature, then it is poured into water containing 20 ml. concentrated sulphuric acid and extracted with ethyl acetate. The organic phases are collected, washed with a saturated aqueous solution of ammonium sulphate, evaporated to dryness and separated by chromatography to give 4.8 g. 1-ethyl-4-benzoyloxypyrrolidin-2-one; m.p. 53°–54° C.; Rf=0.27 (silica gel; eluant ethyl acetate).

EXAMPLE 5

Ethyl 2-(4-acetoxypyrrolidin-2-on-1-yl)-acetate

To a solution of 2 g. ethyl 2-(4-hydroxypyrrolidin-2-on-1-yl)-acetate in 20 ml. anhydrous pyridine is added 0.9 ml. acetyl chloride. The reaction mixture is stirred overnight at ambient temperature, then poured into 50 ml. water containing 14 ml. concentrated sulphuric acid, extracted with ethyl acetate and the organic phases are collected and washed with a saturated aqueous solution of ammonium sulphate, subsequently dried and evaporated to dryness. The residue is chromatographed on silica gel, eluting with diethyl ether, to give 2 g. ethyl 2-(4-acetoxypyrrolidin-2-on-1-yl)-acetate; b.p. 158° C./0.1 mm.Hg; Rf 0.36 (eluant ethyl acetate).

EXAMPLE 6

1-Allyl-4-hydroxypyrrolidin-2-one

To a solution of 5 g. 4-trimethylsilyloxypyrrolidin-2-one in 50 ml. anhydrous acetonitrile are added 12.2 ml. allyl bromide. The solution is warmed to 50° C. and 1.39 g. of 50% sodium hydride (dispersion in mineral oil) are added thereto in small portions. When the addition is completed, the reaction mixture is heated under reflux for 30 minutes, then cooled to ambient temperature and 5 ml. N hydrochloric acid added thereto. The reaction mixture is stirred for 20 minutes and then evaporated to dryness. The residue is chromatographed on a silica gel column, eluting with ethyl acetate, to give 3 g. 1-allyl-4-hydroxypyrrolidin-2-one; b.p. 165° C./0.7 mm.Hg.

EXAMPLE 7

1-Allyl-4-benzoyloxypyrrolidin-2-one

To a solution of 2 g. 1-allyl-4-hydroxypyrrolidin-2-one in 25 ml. anhydrous pyridine are added 1.8 g. benzoyl chloride. The reaction mixture is stirred overnight at ambient temperature, then poured into water containing sulphuric acid, extracted with diethyl ether and the organic phases are collected and evaporated to dryness. The residue is separated by chromatography to give 3.1 g. 1-allyl-4-benzoyloxypyrrolidin-2-one; m.p. 56°–67° C.

EXAMPLE 8

1-(Propyn-2'-yl)-4-benzoyloxypyrrolidin-2-one

Operating as described in the above Examples and using propargyl bromide as the alkylating agent, there is first obtained 1-(propyn-2-yl)-4-hydroxypyrrolidin-2-one, from which is obtained 1-(propyn-2'-yl)-4-benzoyloxypyrrolidin-2-one; m.p. 70°–71° C.

EXAMPLE 9

N-Ethyl-2-(4-hydroxypyrrolidin-2-on-1-yl)-acetamide

Operating as described in Example 1 but using trichlorophenyl bromoacetate instead of ethyl bromoacetate, there is obtained trichlorophenyl 2-(4-hydroxypyrrolidin-2-on-1-yl)-acetate. Five g. trichlorophenyl 2-(4-hydroxypyrrolidin-2-on-1-yl)-acetate are dissolved in 100 ml. methanol, the solution is cooled at 0° C. and 10 ml. ethylamine are added thereto; the reaction mixture is left to stand for 48 hours at ambient temperature, then evaporated to dryness and chromatographed to give 0.4 g. N-ethyl-2-(4-hydroxypyrrolidin-2-on-1-yl)-acetamide; m.p. 84°–86° C.; Rf 0.23 (silica gel; eluant ethyl acetate).

The compounds (I) produced by the process of the present invention are known to display learning memory activity which has been studied mostly utilizing as a comparison compound, Piracetam, the most closely related compound both as to chemical structure and pharmacological behavior. The compounds were studied according to the method described in J. Pharmacol. (Paris) 1972, 3, 1, pages 17–30, in which the animals to be treated were placed at the entrance of a maze filled with cold water (15° C.) at a depth of 24 cm and required to find the exit. A lamp placed at the entrance of the maze helped the animals in getting the right direction. Inside the maze there are a number of compartments which the animals should avoid. The exit is formed by a metal rectangular grate inclined at 45° resting on the bottom.

Male Wistar rats weighing 160–170 g. were used. The animals were placed at the entrance, and once they reached the exit, they ran up the inclined grate to get out of the water. Once out of the maze they were kept one hour in the warmth under an infrared lamp to let them dry, and then put into their cage until the next successive passage in the maze. The compounds to be studied as well as simple saline solutions and the reference compound were administered half an hour before and one hour after each of the two daily trials, that is at 10:00 a.m. and 4:00 p.m. The number of errors and time spent to reach the exit were evaluated and demonstrated that the rats treated with the compounds of the invention learned significantly quicker than the animals treated with the saline solution and with the standard compound.

In the following table the average values ±S.E. obtained in each training session for the compound produced by the invention are given.

| No. animals | TREATMENT | Dose mg/kg and route | Number of errors ± S.E. | | | | |
|---|---|---|---|---|---|---|---|
| | | | Session 1 | Session 2 | Session 3 | Session 4 | Session 5 |
| 40 | Saline | | 18.8 ± 1.2 | 11.6 ± 1.1 | 7.4 ± 0.9 | 5.6 ± 0.9 | 3.4 ± 0.4 |
| 15 | 2-(4-Hydroxy-pyrrolidin-2-on-1-yl)-acetamide | 10 i.p. | 16.5 ± 3.0 | 8.7 ± 1.5 | *3.3 ± 1.0 | *2.7 ± 1.1 | *1.8 ± 0.3 |
| 15 | 2-(4-Hydroxy-pyrrolidin-2-on-1-yl)-acetamide | 10 os | 17.0 ± 2.0 | 8.7 ± 1.6 | *4.6 ± 1.0 | *2.2 ± 0.5 | 2.0 ± 0.4 |
| 15 | piracetam | 30 i.p. | 18.2 ± 1.7 | 9.2 ± 2.0 | 6.8 ± 1.1 | *2.1 ± 0.4 | 2.9 ± 0.9 |

*Significative difference $p < 0.05$

From the above it can be seen that 2-(4-hydroxypyrrolidin-2-on-1-yl)-acetamide at a dose of 10 mg/kg per o.s. is as active as Piracetam at a dose of 30 mg/kg endoperitoneally while at the same dose endoperitoneally it displays an even higher activity than Piracetam at a dose of 30 mg/kg endoperitoneally. Further, the compounds produced by the invention do not display any hypotensive, tranquilizing, muscle relaxant or anticonvulsant activity. At a dose of 200 mg/kg (I.V. on anaesthetized cat) 2-(4-hydroxypyrrolidin-2-on-1-yl)-acetamide has no effect on arterial blood pressure and at the same dose it has no effect on mono- and polysynaptic reflexes while at a dose of 500 mg/kg endoperitoneally it has no effect on the body tone and spontaneous motility (on mouse).

The compounds (I) produced by the present invention improve learning memory and display a protecting effect against the E.E.G. consequence of an overdose of barbiturates and against the reduced performance following brain damage (e.g. cerebral edema).

What we claim is:

1. A process for the preparation of pyrrolidine compounds of the formula:

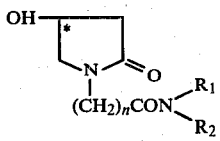
(I)

in which n is 1, 2 or 3 inclusive, $R_1$ and $R_2$, which may be the same or different, are hydrogen or alkyl having 1 to 3 carbon atoms and the asterisk indicates the center of asymmetry of the molecule either as separated enantimoers or as mixture, comprising the steps of (1) reacting γ-amino-β-hydroxybutyric acid in the form of an enantiomer or of a mixture of enantiomers, under anhydrous conditions with a silylating agent, (2) cyclizing the product obtained by heating and (3) then reacting said cyclized product in the presence of an alkaline hydride with an aliphatic acid ester halide of the formula $Hal(CH_2)_nCOOR$, in which Hal is bromine, chlorine or iodine, R is alkyl containing 1 to 4 carbon atoms trichlorophenyl, nitrophenyl or trichloroethyl and n has the same meaning as above, to give a silyl compound of the formula:

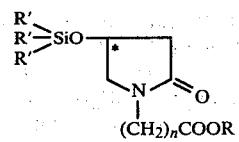
(II)

in which R' is methyl or ethyl and n, R and the asterisk have the same meanings as above, (4) then hydrolizing compound (II) to give the corresponding 4-hydroxy compound and (5) reacting said hydroxy compound with a compound of the formula $R_1.NH.R_2$, in which $R_1$ and $R_2$ have the same meanings as above.

2. A process according to claim 1, wherein the silylating agent is hexamethyldisilazane, bis-(trimethylsilyl)-urea or bis-(trimethylsilyl)-acetamide.

3. A process according to claim 1, wherein the silylating agent is used in the presence of a small quantity of trimethylchlorosilane.

* * * * *